United States Patent [19]

Evans et al.

[11] Patent Number: 4,710,376

[45] Date of Patent: Dec. 1, 1987

[54] TOPICAL THERAPEUTIC COMPOSITION CONTAINING OXIDATION INHIBITOR SYSTEM

[75] Inventors: Sean A. Evans, High Bridge; Eva A. Terpinski, New Brunswick; Douglas Testa, Neshanic Station, all of N.J.

[73] Assignee: Interferon Sciences, Inc., New York, N.Y.

[21] Appl. No.: 697,320

[22] Filed: Feb. 1, 1985

[51] Int. Cl.$^4$ .................... A61K 31/745; A61K 45/02
[52] U.S. Cl. ......................................... 424/83; 424/85
[58] Field of Search ........................... 424/85, 78, 83; 530/351; 435/68

[56] References Cited

U.S. PATENT DOCUMENTS

| | | |
|---|---|---|
| 2,418,938 | 4/1947 | Izard . |
| 2,418,940 | 4/1947 | Izard . |
| 3,485,815 | 12/1969 | Oroslan et al. . |
| 3,914,214 | 10/1975 | Trimnell et al. . |
| 4,098,709 | 7/1978 | Hanauer et al. . |
| 4,137,399 | 1/1979 | Hulsmann et al. . |
| 4,195,128 | 3/1980 | Hildebrand et al. . |
| 4,424,302 | 1/1984 | Block et al. . |
| 4,432,895 | 2/1984 | Tarnowski et al. . |

*Primary Examiner*—Blondel Hazel
*Attorney, Agent, or Firm*—Dilworth & Barrese

[57] ABSTRACT

A substantially non-toxic, stable, topical therapeutic composition is provided which comprises:
(a) a therapeutically active component which is susceptible to oxidative degradation;
(b) an oxidative degradation-inhibitory amount of a redox system containing
 (1) a water soluble polymer containing a plurality of reducing moieties covalently bound thereto and
 (2) a water soluble polymer containing a plurality of oxidizing moieties covalently bound thereto; and
(c) an aqueous vehicle base compatible with the therapeutically active component.

18 Claims, No Drawings

TOPICAL THERAPEUTIC COMPOSITION CONTAINING OXIDATION INHIBITOR SYSTEM

BACKGROUND OF THE INVENTION

This invention relates to compositions containing a therapeutic component which is susceptible to oxidative degradation. More particularly, this invention relates to such compositions especially formulated for topical application in which the oxidation-prone therapeutic ingredient is a proteinaceous biological response modifier such as an interferon or other lymphokine.

Since their discovery in 1957, the interferons, a complex family of several species and multiple subspecies of hormone-like cellular proteins, have been widely investigated for their potent antiviral, antiproliferative and immunomodulating properties.

The major interferon species are now designated alpha, beta and gamma according to their origin and mode of induction. Leukocytes are the primary producers of the alpha species, fibroblasts mainly that of the beta species and T lymphocytes are the principal source of the gamma species. Collectively, the alpha and beta interferons are classified as Type I interferons, Type II being immune interferons. Each of these interferon species have been produced on an industrial scale employing recombinant techniques in bacteria and yeast with purification being accomplished by means of classical techniques or by monoclonal immunosorbent antibody. General discussions of these interferons can be found in various texts and monographs, including *The Interferon System*, by W. E. Stewart, II, Springer-Verlag, New York (1979); *Interferon* 1981, Vol. 3, edited by Ion Gresser, Academic Press, New York (1981); and *Interferon Therapy*, World Health Organization Technical Reports Series 676, World Health Organization, Geneva, 1982.

For over a decade, interferons of all types have been employed in clinical trials. Originally, they were applied against viral pathogens, but subsequently their use has been extended to include treatment of a variety of malignant diseases An important factor in the clinical application of interferons and other lymphokines is the method of administration. Systemic administration, by either intravenous of intramuscular injection, has been used most frequently with some success. Among the problems inherent in this method of administrations is that the interferon can come into contact with uninfected or nonmalignant cells causing unwanted side effects. Accordingly, the preferred approach would be to deliver interferon directly to the affected tissues or organs. In some cases, this can be accomplished by direct injection into the diseased site. In other cases, e.g., eye disease and diseases like herpes genitalis, herpes labialis, herpes zoster and adenovirus induced keratitis and condyloma, all of which produce skin lesions, local topical application is the preferred method of administration. The topical administration of interferon has proved to be a formidable problem for a number of reasons. First, interferon is a protein with a higher molecular weight than the molecular weights of therapeutic agents previously administered in topical preparations, e.g., procaine, nitroglycerin, etc. In general, large molecular weight proteins have a much smaller solution diffusion coefficient than low molecular weight substances, a difference which generally becomes exacerbated in semi-solid media. Accordingly, the vehicle used to administer interferon locally must be able to hold the high molecular weight interferon in suspension during packaging, shipping and application, and yet also be able to release the interferon from the vehicle in a reasonable length of time once it has been applied to the diseased site. Second, the vehicle must not adversely affect the activity of the interferon by direct chemical action, precipitation or immobilization, any of which would preclude interaction of the interferon with the diseased site.

Third, and in many ways the most difficult objective to achieve, the vehicle should allow the interferon preparation a sufficiently long shelf-life at room and body temperatures to allow for convenient shipping, handling and administration by the patient. In general terms, if a therapeutic agent is to be administered topically, the agent and its vehicle should satisfy the following shelf-life conditions: (1) the agent should retain a significant fraction of its therapeutic effect when held at room temperature (e.g., about 22° C.) for a period of approximately fourteen days and (2) the agent should also retain a significant fraction of its activity when held at body temperature (37° C.) for a period of approximately one day. The fourteen day requirement at room temperature allows for shipping, handling and retailing of the preparation. The one-day requirement at body temperature allows the patient to carry the product on his person and apply it throughout the day when needed.

Interferons produced by recombinant-DNA techniques or from natural sources when in a crude or partially purified form are notoriously temperature-labile substances.

For example, Moller, et al. reported at the Third Annual International Congress for Interferon Research that even at 4° C., a human leukocyte interferon gel lost 80% of its activity in just two weeks. (Moller, B. R., Johannesen, P., Osther, K., Ulmsteen, U., Hastrup, J. and Berg, K., "Initial Evaluation of Topical Treatment of Dysplasia of the Cervical Epithelium with a Human Leukocyte Interferon Gel,", Third Annual International Congress for Interferon Research, 1982.) Plainly, this is far from the fourteen days at 22° C. and one day at 37° C. stability requirements which an interferon preparation should achieve to satisfy commercial requirements. Presently available data suggest that highly purified interferon, in particular, highly purified gamma-interferon, may also be temperature-labile. The problem of temperature-related instability of the lymphokines generally and the interferons in particular is further aggravated by the tendency of these proteinaceous therapeutics to undergo oxidative degradation both during storage and during application. In the case of topical preparations, the tendency toward oxidative degradation is particularly troublesome since it is difficult, if not impossible, to exclude those conditions, e.g., the presence of atmospheric oxygen, which make such degradation possible once the preparation has been applied to the diseased site.

While it might appear to be a simple enough solution to this problem to add an antioxidant to the topical preparation to inhibit or forestall oxidative degradation of the active therapeutic component therein, in practice this is not an acceptable approach with many known antioxidant agents which tend to be somewhat toxic (even if only mildly so) and, being of relatively low molecular weight, are readily absorbed through the skin. (For various types of antioxidants which are commercially available, reference may be made to Kirk-Othmer, *The Encyclopedia of Chemical Technology*, 3rd Ed., Vol. 2, pp. 132–141.) Even aside from the problem of toxicity, it is generally undesirable to treat with a drug composition containing any bio-active component which is not absolutely essential to achieve the desired therapeutic effect.

Accordingly, the monomeric interferon composition of U.S. Pat. No. 4,432,895 containing a reducing and oxidizing agent, i.e., a redox reagent, such as cysteine and cystine, cysteamine and cystamine, and the like, might not be a likely candidate for a preparation to be applied topically. Indeed, U.S. Pat. No. 4,432,895 makes provision for the removal of the redox reagent from the interferon composition prior to its therapeutic use by known chromatographic procedures or by dialysis.

In view of this state of the art, it is clear that a vehicle for use in topically administering interferon or other drug susceptible to oxidative degradation has a heavy burden to carry in terms of providing a toxicologically acceptable and therapeutically stable preparation.

SUMMARY OF THE INVENTION

It is an object of the present invention to overcome the problems in the prior art regarding providing suitable vehicles for the topical administration of therapeutic compositions containing an active ingredient which is susceptible to oxidative degradation.

It is a particular object of the present invention to provide topical administration vehicles for proteinaceous drugs such as the lymphokines, and especially the interferons, which will hold the drug in suspension during packaging, shipping and application and yet will readily release the drug at the diseased site.

It is still another object of the invention to provide topical administration vehicles which do not significantly diminish the activity of the therapeutically active component therein by direct chemical action, precipitation, immobilization or other mechanisms, both during manufacture of the preparation and thereafter.

It is a further particular object of the invention to provide interferon topical administration vehicles in which the interferon exhibits an extended shelf-life at both room temperature and body temperatures. More particularly, it is an object of the invention to provide interferon topical administration vehicles in which the interferon maintains a substantial fraction of its biological activity for a period of approximately fourteen days or longer at room temperature and approximately one day or longer at body temperature.

In accordance with the present invention, the foregoing and other objects are achieved by providing a substantially non-toxic, stable topical therapeutic composition which comprises:

(a) a therapeutically active component which is susceptible to oxidative degradation;

(b) an oxidative degradation-inhibitory amount of a redox system containing (1) a water soluble polymer containing a plurality of reducing moieties covalently bound thereto and (2) a water soluble polymer containing a plurality of oxidizing moieties covalently bound thereto; and, (c) an aqueous vehicle base compatible with the therapeutically active component.

Topical therapeutic compositions formulated with a redox system in accordance with the teachings of this invention retain high levels of therapeutic effectiveness despite relatively lengthy periods of storage and/or application to a diseased site. Due to the relatively large size of the water soluble polymer molecule which in effect serves as an "anchor" for the oxidizable and reducible moieties constituting the active principle of the redox system, there will be little tendency of these moieties to be absorbed through the skin where the topical therapeutic composition is applied. Such would not be the case where the moieties were present in the composition in their chemically uncombined form; their relatively small molecular size would permit them to pass through the skin in appreciable quantities thus presenting the risk of toxic or other undesirable side effects.

DESCRIPTION OF THE PREFERRED EMBODIMENTS

The present invention can be practiced with any therapeutic agent which is intended for topical application and which is prone to a loss in potency due to oxidative degradation. In general, the stability of topical therapeutic compositions containing proteinaceous substances as the active ingredient can be significantly improved by incorporating a redox system as taught herein.

The lymphokines represent a particularly important class of proteinaceous therapeutics which are advantageously formulated into topical preparations as described herein. Of the lymphokines which have been studied to date, the interferons have received the greatest amount of attention from the medical and scientific communities and therefore the present invention will be hereinafter illustrated with specific reference to them. However, it shall be understood that the teachings herein as applied to the interferons apply as well and to the same extent to any other therapeutic substances which are susceptible to oxidative degradation.

The invention is applicable to all types of interferons including natural interferons, interferons produced by recombinant DNA technology, and interferons produced by chemical synthesis. Also, the invention can be used with crude, semi-purified and purified interferons. Examples of the more common types of interferons with which the invention can be used include alpha, beta and gamma interferons of human and animal origin. Each of these three types of interferons can be produced by a variety of techniques. For example, a method for producing alpha-interferon is described by Cantell, et al. in *Methods in Enzymology*, Vol. 78, pages 29–38 (1981). Similarly, beta-interferon production schemes are described by Leong and Horoszewicz in *Methods in Enzymology*, Vol. 78, pages 87–101 (1981), and by Van Damme and Billiau in *Methods in Enzymology*, Vol. 78, pages 101–119 (1981). A method for producing gamma-interferon is described by Johnson, et al. in *Methods in Enzymology*, Vol. 78, pages 158–162 (1981). A particularly preferred method for producing gamma-interferon is described in U.S. patent application Ser. No. 446,160, filed on Dec. 2, 1982, and assigned to the same assignee as the present invention. The pertinent portions of the foregoing references and patent applications are incorporated herein by reference.

In general, interferon produced by these and other methods is supplied as a liquid.

The amount of interferon which is topically administered in any particular case, as well as the frequency at which the interferon is administered, will depend upon such factors, well known to the art, including the interferon used, the disease being treated and the patient's response to interferon treatment.

For alpha and beta interferons, unit strengths have been established by the National Institutes of Health (United States Department of Health and Human Services, Bethesda, Maryland). In terms of these unit strengths, dosage levels for ointment preparations using crude or partially purified natural interferons can range from about 10,000 NIH Units/gram of ointment to 1,000,000 NIH Units/gram, while for purified natural and recombinant DNA interferons, the dosage levels can be as high as 50,000,000 NIH Units/gram. Preferred dosage levels for alpha and beta interferons in ointments are generally between about 25,000 and about 500,000 NIH Units/gram of ointment.

The conveniently obtained dosage levels for liquid preparations exhibit a similar variability as a function of the source of the interferon used. Thus, a formulation including crude or partially purified natural alpha or beta interferons can have a strength of between approximately 25,000 and 2,000,000 NIH Units per milliliter of preparation, with a particularly preferred dosage level being between approximately 100,000 and 1,000,000 NIH Units per milliliter. If desired, even higher levels, e.g., 50,000,000 NIH Units/milliliter, can readily be obtained with purified natural and recombinant DNA interferons.

For gamma-interferon, unit strengths have not yet been established. Gamma-interferon is commercially available from a number of sources, including Interferon Sciences, Inc., (New Brunswick, New Jersey), the assignee of the present application, and Meloy Laboratories (Springfield, Virginia.) The strengths of these commercial preparations are given in units established by in-house standards. In terms of these units, ointment and liquid gamma-interferon preparations generally contain similar concentration levels to those given above for alpha and beta interferons.

In addition to applying one interferon at a time, the present invention is also applicable to the administration of mixtures of interferons, including interferons of different types, interferons from different sources and interferons produced by different methods of manufacture. For example, it is known that alpha and beta interferons, as well as possibly other interferon combinations, e.g., mixing different recombinantly produced alpha-interferons, can have a synergistic effect. The present invention specifically encompasses the topical administration of such synergistic combinations.

As previously stated, the oxidative degradation-inhibitor component of the topical preparations herein comprises a redox system containing a reducing agent and an oxidizing agent. Both the reducing agent and the oxidizing agent are provided in the form of water soluble polymers which have been chemically modified in known and conventional ways to contain the reducing and oxidizing moieties covalently bound thereto. As used herein, the term "polymer" shall be inclusive of homopolymers as well as random, block and graft copolymers.

Examples of water soluble polymers which can be modified to contain reducing and oxidizing moieties in accordance with this invention include any of the water soluble cellulose ethers, in particular, carboxyethyl cellulose and carboxymethyl cellulose; mixed ethers such as carboxyalkylhydroxyalkyl ethers, e.g., carboxymethyl hydroxyethyl cellulose; hydroxyalkyl celluloses such as hydroxyethyl cellulose and hydroxypropyl cellulose; alkyl hydroxyalkyl celluloses such as methyl hydroxypropyl cellulose; alkyl celluloses such as methyl cellulose, ethyl cellulose and propyl cellulose; alkyl carboxyalkyl celluloses such as ethyl carboxymethyl cellulose; cellulose sulfate esters, e.g., those disclosed in U.S. Pat. Nos. 3,702,843 and 4,141,746; polyacrylamide homopolymers and copolymers such as those described in U.S. Pat. Nos. 3,702,843 and 4,141,746; polyacrylamide homopolymers and copolymers such as those described in U.S. Pat. Nos. 2,625,529; 2,740,522; 2,729,557; 2,831,041; 2,909,508; 3,818,998; and, 4,103,742; guar gum; heteropolysaccharides such as those produced by fermentation of carbohydrates by *Xanthomonas campestris, Xanthomonas begonia, Xanthomonas phaseoli, Xanthomonas hederae, Xanthomonas incanae, Xanthomonas carotae* and *Xanthomonas translucens;* polyalkylene glycols, e.g., those of the formula $HO(CH_2CH_2O)_nH$ wherein n can vary from about 20 to about 225,000; polymethacrylic acid olefin-maleic acid copolymers; amino-containing polymers such as polyethyleneimine, polyinyl amine, and the like; polyvinyl alcohol, and the like. The molecular weights of the suitable water soluble polymers and copolymers can vary widely.

Hydroxyethyl cellulose (HEC) is especially advantageous in that it is approved for use in pharmaceutical formulations and also serves as a thickener for aqueous-based media such as the topical therapeutic compositions herein.

The monomeric units (400 to 10,000 or more) comprising the HEC molecule can be represented by the structure:

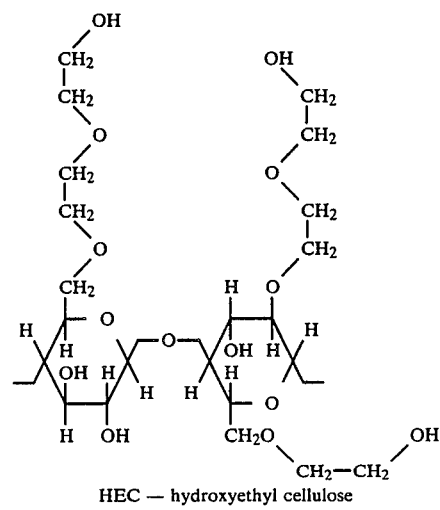

HEC — hydroxyethyl cellulose

While all of the hydroxyl groups are available for reaction, there is a greater likelihood of reaction at the hydroxyl groups which terminate the ethoxy ether chains. The terminal hydroxy groups of HEC can be reacted directly with a reducing/oxidizing agent to covalently bind the agent to the polymer. For example, HEC can be reacted with a reducing/oxidizing agent possessing at least one carboxylic acid group under esterification conditions to bind the agent to the polymer through ester linkages. Alternatively, the hydroxyl groups of the HEC can first be modified with a difunctional intermediate, e.g., a dicarboxylic acid such as maleic acid, to provide pendant carboxylic acid groups, the latter then being reacted with a reducing/oxidizing agent possessing a reactive group such as a hydroxy, thiol or amine group. Other procedures for preparing functionalized celluloses which can be sued herein are described in U.S. Pat. No. 4,137,399. These direct and indirect chemical procedures whereby reducing/oxidizing moieties can be covalently bound to HEC apply with obvious modifications to other water soluble polymers including those previously cited above.

Reducing agents which can be used herein include amines such as 6-ethoxy-1,2-dihydro-2,2,4-trimethylquinoline, N,N'-diphenyl-p-phenylenediamine, N,N'-di-beta-naphthyl-p-phenylenediamine and alkylated diphenylamines such as monooctyl diphenylamine and dioctyl diphenylamine; phenols such as the alkylated hydroquinones and the bisphenols; mercaptoethanoic mercaptans such as mercaptoethanoic acid, mercaptopropionic acid, dithioglycerine, glutathione, pantetheine, mercaptoethanol, dithiothreitol, thioglycolic acid and thiosorbitol, reduced alpha-amino acids such as cysteine, cysteamine, and the like.

The disulfides constitute a particularly advantageous class of reducing agents which can be used to modify the foregoing water soluble polymers. In addition to the preferred disulfide, dithiodipropionic acid, which possesses the structure

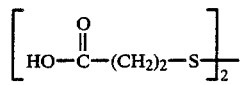

other suitable disulfides for the practice of this invention include those of the structures:

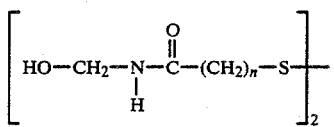

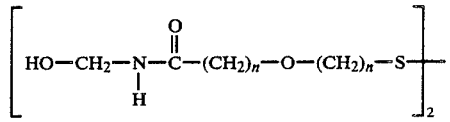

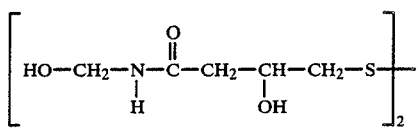

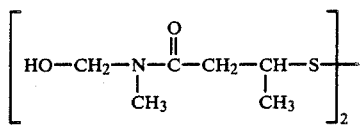

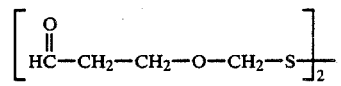

wherein n is an integer of from 1 to about 10. Direct or indirect methods of covalently bonding these additional disulfides to the backbone of the water soluble polymer can be utilized as previously explained. While monomeric functionalized thiol groups can be used, it is necessary to protect the thiol group with a blocking agent employing known procedures (e.g., those described in Milkowski, et al. *Organic Synthesis.* 59, 190 (19 ); Pastuszak, et al. *J. Am. Chem. Soc.,* 46, 1868 (1981); Veber, et al. *J. Am. Chem. Soc..* 94, 5456 (1972); Marbach, et al. *Helv. Chem. Acta,* 57, 403 (1974); and Ruegg, et al. *Biochem. J.,* 1979, 127 (1979) followed by deprotection to provide the free thiol oxidizing agent.

In the oxidized form, the foregoing can serve as the oxidizing moieties of the water soluble polymers herein. For example, in the case of a preferred reducing agent, dithiodipropionic acid, reacted with a preferred water soluble polymer, HEC, the resulting polymer can take any and all of the following forms (only monomeric units shown):

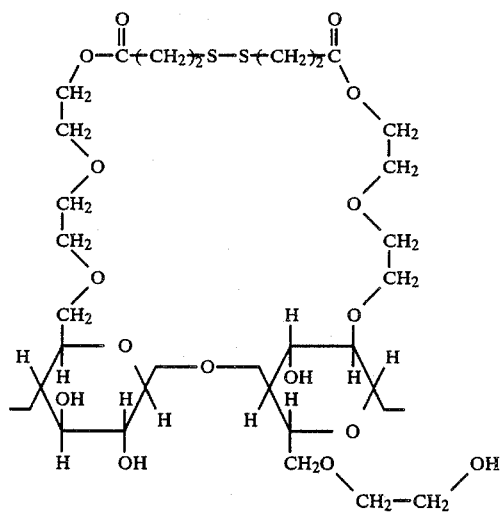

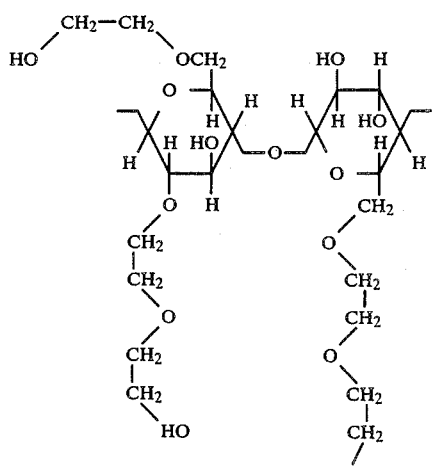

HEC — intramolecular dithiodipropionic acid ester
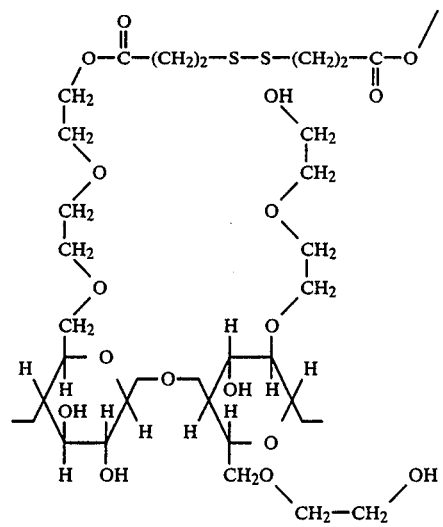
HEC — intermolecular dithiodipropionic acid ester
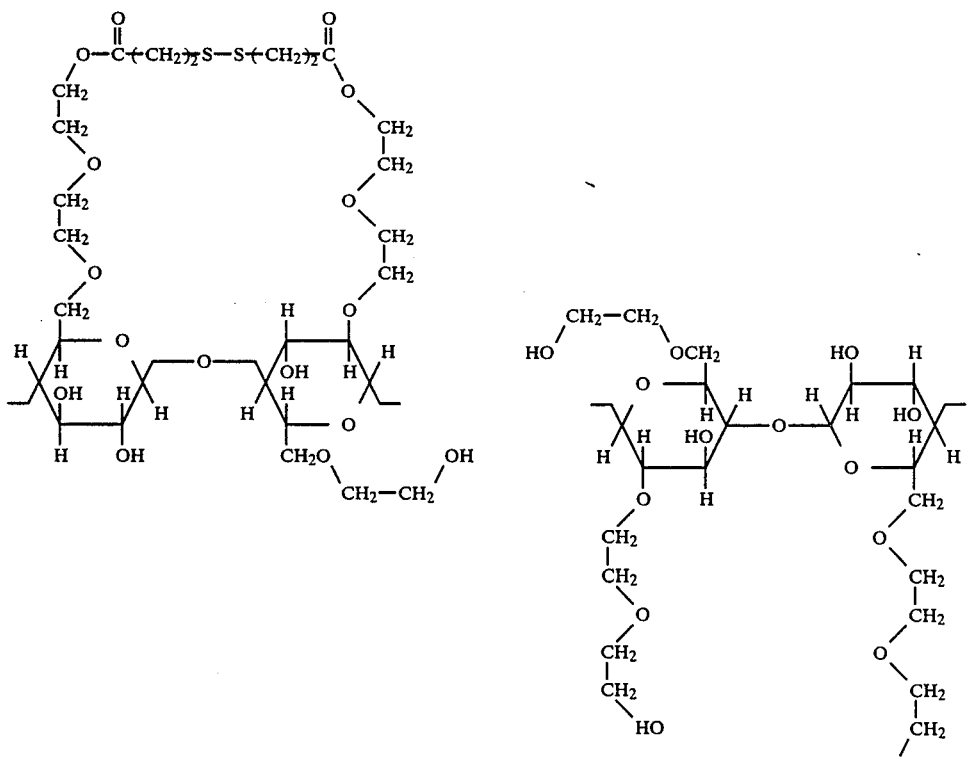

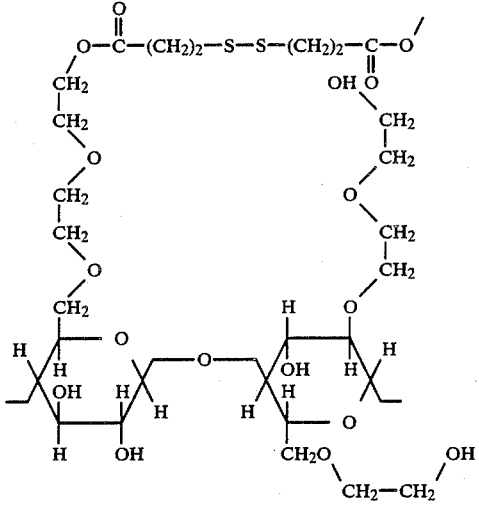

HEC — mixed intramolecular/intermolecular dithiodipropionic acid ester

Cellulose polymers which have been modified to contain disulfide groups are known from U.S. Pat. Nos. 2,418,940, 2,418,938 and 3,485,815 and can be prepared by the methods which are disclosed therein.

Upon undergoing reduction, the disulfide linkage in each of the above forms will be disrupted thereby providing the following reducing component of the redox system herein (only monomeric unit shown):

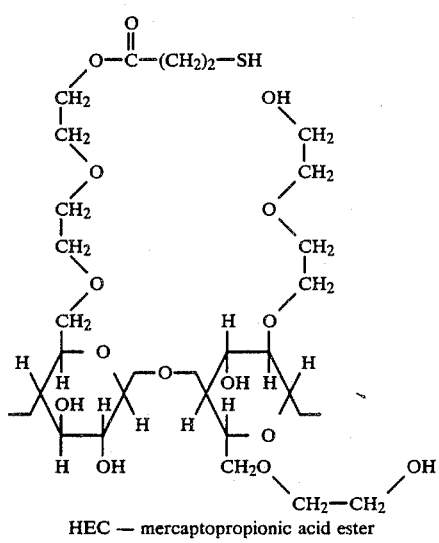

HEC — mercaptopropionic acid ester

The reducing moieties of the redox system, such as the one shown above, upon undergoing oxidation, will form the disulfide linkage.

In much the same way, the other reducing moieties herein will undergo oxidation to provide the oxidizing moieties of the redox system.

In the case of the interferons, the active forms of which comprise a chain of 165 amino acids and one or two disulfide bridges, it is necessary to maintain a balance between the polymeric reducing agent and the polymeric oxidizing agent such that the reducing agent can intercept any oxygen which would otherwise get at the interferon causing it to degrade and the oxidizing agent will help to preserve the disulfide bonds of the active forms of interferon. The ratio of reducing agent to oxidizing agent is not critical, the optimum ratio for a particular interferon composition being readily determined by those skilled in the art employing routine laboratory procedures. In general, a molar ratio of reducing moieties to oxidizing moieties in the range of from about 30:1 to about 1:1 and preferably from about 10:1 to about 2:1 can be used with good results.

The amount of redox system necessary to impart significantly improved stability against oxidative degradation can vary widely with from about 0.00001 moles to about 0.02 moles redox system per 10 to 40 ml of interferon source liquid being suitable in most cases.

The aqueous vehicle base used with the present invention must simultaneously satisfy the following criteria; (1) it must be capable of holding the high molecular weight interferon or interferons in suspension and yet be able to release the interferon or interferons at the diseased site, (2) it must be compatible with the interferon or interferons being administered so that the activity of the interferon is not adversely affected, (3) it must be acceptable to the patient, i.e., it should be non-irritating, non-toxic and should have an appropriate odor, color and texture and (4) it must have suitable rheological properties so that it can be easily manufactured and dispensed into containers and subsequently applied to the diseased site by the patient.

The topical therapeutic compositions herein can advantageously be formulated with a water soluble polyalkylene glycol, a particularly preferred class of which is the polyethylene glycols. By combining different molecular weight polyethylene glycols, e.g., polyethylene glycols having molecular weights between 300 and 20,000, a wide range of viscosities and aqueous solution capacities (e.g., 15–25%) for this type of base can be obtained. One such formulation comprises a 60:40 mixture of a 400 molecular weight polyethylene glycol and a 3350 molecular weight polyethylene glycol. This mixture produces a particularly suitable vehicle base for administering interferons.

To use these preferred polyethylene glycol-containing bases with interferons, however, requires special handling procedures for incorporating the interferon into the vehicle base. At room temperature and below, the various mixtures of polyethylene glycols preferred for use with the present invention are semi-solid pastes rather than liquids. In contrast, interferons, as stated above, are typically supplied as liquids. The two components can be combined by mechanical mixing but such mixing often results in a non-homogeneous ointment and can denature the interferon. In accordance with the invention and as described in more detail in connection with the example presented below, it has been found that a superior polyethylene glycol-based ointment can be prepared by combining the interferon with the polyethylene glycols when both components have been heated to an elevated temperature, e.g., 45° C. Surprisingly, it has been found that this procedure does not significantly deactivate the interferon, notwithstanding its proteinaceous character, which one would expect would lead to heat sensitivity.

In order to maintain the consistency of the final preparation within a suitable range for application to the diseased site, it has been found that the amount of interferon source liquid added to polyethylene glycol vehicles bases such as the 60:40 base described above should be kept in the range of from about 0.01 to about 0.25 milliliters per gram of base, and most preferably in the range from about 0.05 to about 0.15 milliliters per gram of base.

Another particularly preferred water-soluble vehicle base for use with the present invention employs hydroxethyl cellulose as a thickening agent for the topical preparation. The HEC gel can be prepared as follows: the polymer powder is wetted and dispersed in glycerin as a suspended slurry, the liquid phase which can include the interferon source liquid is added to the slurry and after a short period with gentle agitation, a gel which thickens into a homogenous mixture is obtained. Further addition of liquids, including the interferon source liquid, to the already formed gel will be eventually absorbed with slow mixing.

Since, as discussed above, interferons are normally supplied as liquids, this means that a homogeneous mixture can be easily obtained. Also, it has been found that hydroxyethyl cellulose-containing vehicle bases, after they fully gel, give the final preparation a pleasing feel and appearance. Moreover, interferon preparations using this vehicle base have been found to have especially high initial interferon titers.

A preferred topical ointment base using hydroxethyl cellulose includes between about 1 and about 5 weight percent of hydroxyethyl cellulose, for example, a viscosity of 2200 centipoise, between about 10 and about 50 weight percent of glycerine and between about 49 and about 85 weight percent of water. To this vehicle base is preferably added between about 10 and about 40 milliliters per hundred grams of base of interferon source liquid. A particularly preferred hydroxyethyl cellulose vehicle base includes between about 2 and about 3 weight percent of hydroxyethyl cellulose, between about 20 and about 38 weight percent of glycerine and between about 60 and about 78 weight percent of water. In combination with this base, preferably between about 15 and about 20 milliliters of interferon source liquid are used per hundred grams of base. For interferon source liquids having low titers, the quantity of water used in the vehicle base can be reduced and higher amounts of source liquid can be admixed with the base. In this way, the titer of the final preparation can be adjusted without adversely affecting the preparation's rheological properties. In place of glycerine and water, the hydroxethyl cellulose-containing vehicle base can include polysorbate and other similar wetting agents. Instead of HEC, other celluloses and their derivatives, such as sodium CMC, methylcellulose and hydroxypropyl cellulose can be used.

In addition to an interferon component and an aqueous vehicle base component, the topical preparations of the present invention can optionally include one or more protease inhibitors. These inhibitors can be included in the preparations for the purpose of reducing the rate of decay of the biological activity of the interferon component due to proteolytic agents. The major source of interferon decay in topical preparations, especially at elevated temperatures, i.e., room or body temperature, is digestion of the interferon by proteolytic enzymes introduced into the preparation as part of the interferon source liquid. Once in the preparation, these contaminating enzymes over time destroy the therapeutic potency of the interferon.

The proteolytic enzymes found in interferon source liquids come from the human serum, leukocytes or other biological materials used to manufacture the interferon, as well as possibly from contaminating microorganisms. Typically these enzymes are of the "serine" protease type in that they have a critical serine residue at their active site. Examples of such proteolytic enzymes include trypsin, plasmin, thrombin, leukocyte elastease, kallikrien, and cathepsin. In some cases (e.g., plasmin and thrombin), the interferon source liquid may not actually include the active proteolytic enzyme, but rather, an inactive precursor which is slowly converted to the active form, especially at elevated temperatures.

To control the effects of these proteolytic enzymes, the topical preparations of the present invention advantageously include one or more protease inhibitors which interact with the proteolytic enzymes and prevent them from digesting and thus inactivating the interferon in the interferon source liquid.

Various proteolytic inhibitors of human, animal or plant origin can be used in the practice of the present invention. Because of the highly conserved nature of both protease inhibitors and the active sites of the proteolytic enzymes typically present in interferon source liquids, the inhibitor need not be from the same species as the proteolytic enzyme, but can be from a different species or even of plant origin. For example, soybean trypsin inhibitor (also referred to herein as "soybean inhibitor" and abbreviated "STI") is capable of inhibiting trypsins from such diverse sources as humans, cows, salmon, stingrays, barracudas and turkeys. Also, in addition to inhibiting trypsins, STI will inhibit bovine and chicken chymotrypsin, human plasmin, human kallikrein and cocoonase, as well as blocking the conversion of prothrombin to thrombin.

Protease inhibitors particularly preferred for use with the present invention include STI, alpha$_1$-trypsin inhibitor (hereinafter abbreviated alpha$_1$-AT), N$^{alpha}$-tosyllysine chloromethyl ketone (hereinafter abbreviated "TLCK"), phenylmethylsulfonyl fluoride (hereinafter abbreviated "PMSF"), N$^{alpha}$-tosylphenylalanine chloromethyl ketone (hereinafter abbreviated "TPCK"), alpha-2-macroglobulin, and mixtures thereof. Of these inhibitors, STI is particularly preferred because of its low cost and alpha$_1$-AT is most preferred, especially when prepared from human serum, because of the reduced chance of allergic reactions. A suitable technique for purifying human alpha$_1$-AT is described by J. Travis, et al. in *Methods in Enzymology*, 80, pages 754–765. The other preferred protease inhibitors listed above are commercially available from various sources including Sigma Chemical Company, St. Louis, Mo. (STI, TLCK, and PMSF), Chemical Dynamics Corp., South Plainfield, N.J. (TPCK) and Boehringer Mannheim Biochemicals, Ind., Indiana (alpha-2-macroglobulin).

The amount of protease inhibitor which can be included in the topical preparation depends upon the amount and type of proteolytic enzyme present in the interferon source liquid, and the particular inhibitor used. For example, crude alpha-interferon sold by Interferon Sciences, Inc. (New Brunswick, N.J., Catalog #1100) following concentration in a known and conventional manner typically contains approximately 100 mg of protein per milliliter of liquid. Of this 100 milligrams, up to 1% may be proteolytic enzymes generally of the type found in human plasma (e.g., thrombin, plasmin, etc.). These enzymes have molecular weights in the range of 25,000 to 100,000 daltons. In comparison, STI, for example, has a molecular weight of approximately 20,000 daltons. Accordingly, since this inhibitor generally forms a 1:1 complex with its target proteolytic enzymes, the addition of 1 mg of inhibitor per milliliter of interferon source liquid can be expected to produce a multifold molar excess of STI on the order 0.25 milligrams per milliliter of crude concentrated alpha-interferon source liquid is sufficient to guarantee an extended interferon half-life, especially at elevated temperatures, such as, 37° C. Since this particular interferon source liquid has an activity of approximately $2 \times 10^6$ Units per milliliter and since it is preferable to have between 25,000 and 500,000 Units per gram of ointment, this means an STI addition rate of between approximately 0.003 and 0.06 milligrams inhibitor per gram of ointment. ([25,000 Units/gram]/[$2 \times 10^6$ Units/ml]×[0.25 mg/ml]=0.003 mg/gm; [500,000 Units/gram]/ $2 \times 10^6$ Units/ml]×[0.25 mg/ml]=0.06 mg/gm). Similarly, for a liquid preparation using this particular interferon source liquid and having a strength of between 200,000 and 2,000,000 Units per milliliter of preparation, between approximately 0.025 and 0.25 milligrams of this inhibitor is used per milliliter of solution. ([200,000 Units/ml]/[$2 \times 10^6$ Units/ml]×[0.25 mg/ml]=0.025 mg/ml; [2,000,000 Units/ml]/[$2 \times 10^6$ Units/ml]×[0.025 mg/ml]=0.25 mg/ml).

As will be evident to persons of ordinary skill in the art, a similar procedure to that described above can be used to determine the appropriate addition levels for other inhibitors and other interferon source liquids.

In addition to including one or more interferons and a vehicle base, the interferon preparations of the present invention can include various optional components. For example, it is generally desirable to include one or more preservative in the preparation to prevent microbial growth. Examples of preservatives which have been found compatible with interferons include benzalkonium chloride and methyl and propylparabens. Also, the preparations can include non-interferon type therapeutic agents in addition to the one or more interferons. Other optional components which can be included in the preparation are various coloring agents and protein stabilizing agents such as glycerol, sucrose, sorbitol and mannitol.

Of the following examples, Examples 1 to 3 are illustrative of the preparation of the water soluble polymeric reducing and oxidizing agents comprising the redox system herein and Examples 4 to 6 are illustrative of various topical interferon compositions containing polymeric redox systems in accordance with this invention.

EXAMPLE 1

This example illustrates the preparation of HEC-cysteine hydrochloride reducing agents of different cysteine content.

Hydroxyethyl Cellulose (10 g) was dissolved in 500 ml water. A water solution of cysteine hydrochloride monohydrate was added to the stirred HEC solution and the resulting solution was refluxed under nitrogen for three hours. Water was removed under vacuum and dry product was ground in a mill. Four water soluble polymer compounds differing in cysteine hydrochloride content were obtained:

| Polymer Compound | m.p. [°C.] | Active Cysteine Contents [W/W %] |
|---|---|---|
| 1 | 150–160 (d) | 24.6 |
| 2 | 170–180 (d) | 8.1 |
| 3 | 190–220 (d) | 4.3 |
| 4 | 240–270 (d) | 0.9 |

Compounds 1–4 were titrated with iodine and thiosulfate solution in order to determine the reducing activity of the products as well as the amount of active SH groups in a given amount of product. All compounds demonstrated significant reducing activity. In addition, Compound 1 was dialyzed against water under nitrogen to determine its stability; the dialyzed product (m.p. 215°–220° C.) remained active as a reducing agent after three days of dialysis.

EXAMPLE 2

This example illustrates the preparation of an HEC-cystine hydrochloride oxidizing agent. Both reactions were carried out in dimethyl formamide (DMF) solution. In the case of the second reaction, a reducing agent was added; the first compound was obtained without a reducing agent. Reducing agents which are used to rupture the disulfide crosslinks and to form mercapto groups can be any of the following compounds: sodium tetraborate, dithiothreitol, dithioerythritol, glutathione, mercaptoethanol, 2,3-dimercaptoproponal, thioglycolate and thioglycolic acid. The compounds were obtained in the following way:

Polymer Compound 5

HEC (10 g) was dissolved in 250 ml of DMF. Cystine hydrochloride was added into a stirred solution followed by addition of thionyl chloride in DMF. The reaction mixture was stirred and heated on a water bath for 4 hours and left overnight. Half of the DMF was removed under vacuum and the resultant solution was dialyzed against water under nitrogen. The product was dried under vacuum, m.p. 218°14 219° C.

Polymer Compound 6

The reaction mixture obtained as described above was alkalized with 1N NaOH and an aqueous solution of NaBH$_4$ reducing agent was introduced. When the evolution of hydrogen ceased (0.50–1.0 hr.), 1N HCl was added to decompose excess NaBH$_4$. Half of the solvent was removed under vacuum and the resultant solution was dialyzed against water under nitrogen. The product was dried under vacuum, m.p 216°–218° C.

Reducing activity of these compounds was observed with iodine solution. Compound 5 did not exhibit reducing activity whereas Compound 6 exhibited significant reducing activity.

EXAMPLE 3

This example illustrates the preparation of HEC-dithiodipropionic acid ester reducing agent.

Dithiodipropionic acid (5 g) was heated on a water bath with thionylchloride (15 ml) for 5 hours. Two drops of DMF were added. Excess thionyl chloride was removed under vacuum. HEC (10 g) was dissolved in 250 ml of DMF and dithiodipropionyl chloride in DMF was dropped into the stirred solution. The reaction mixture was heated for 5 hours and left overnight.

It was then alkalyzed with 1N NaOH followed by introduction of an aqueous solution of $NaBH_4$ with stirring for one hour. Excess $NaBH_4$ was decomposed with 1N HCl and half of solvent was removed under vacuum. The resultant solution was dialyzed against water under nitrogen. The product was dried under vacuum, m.p. 230°–235 ° C. The product exhibited significant reducing activity.

EXAMPLE 4

Preparation of Crude Concentrated alpha-Interferon Source Liquid

Crude concentrated alpha-interferon source liquid was prepared from Natural Crude alpha-Interferon sold by Interferon Sciences, Inc., (New Brunswick, N.J., Catalog #1100) as follows. The pH of the commercial product was checked and, if necessary, adjusted to 7.0–7.2 using sodium hydroxide. The pH adjusted material was then concentrated using a hollow fiber filter having a 10,000 molecular weight cutoff and run at 20 p.s.i. until the volume of the product was 1/50 of the starting volume. The concentrated product was then clarified by centrifugation at 18–20,000×g and finally sterile filtered.

EXAMPLE 5

Preparation of an Interferon Topical Ointment Having a Polyethylene Glycol Vehicle Base An interferon ointment having a polyethylene glycol vehicle base is prepared as follows.

Sixty grams of polyethylene glycol 400 liquid and 40 grams of polyethylene glycol 3350 powder, both obtained from Fisher Scientific, Fair Lawn, N.J., are mixed together in a sterile glass beaker and then autoclaved at 121° C. for 40 minutes. While still molten, the beaker is submerged in a 50° C. water bath set inside a laminer flow hood. The mixture is slowly stirred with a sterile propeller-type stirring blade and its temperature was adjusted to approximately 45° C. Fifteen milliliters of frozen crude concentrated alpha-interferon source liquid prepared in accordance with Example 4 above is thawed at 4° C. and then heated in a water bath to a temperature of approximately 45° C. The interferon is then added to the molten polyethylene glycol mixture and the two components are stirred together. Thereafter, 4 gm of redox system containing 2.0 gm of PEG-thiopropionic acid (1% thiopropionic acid bound) oxidizing agent and 2.0 gm of PEG - dithiodipropionic acid (0.1% thiopropionic acid bound) reducing agent are combined with the polyethylene glycol-interferon mixture. Stirring is resumed and continued until the mixture is homogeneous and has an even color.

Using a syringe, pipet or equivalent, aliquots of the interferon/polyethylene glycol mixture are placed in sterile aluminum ointment tubes which have been pre-chilled to 4° C. The open ends of the tubes are covered with alcohol-swabbed parafilm and the tubes are placed in a −20° C. freezer. After approximately 20 minutes at −20° C., the tubes are crimped under a laminer flow.

To fill a large number of tubes, it has been found preferable to perform the filling step in batches so as to minimize the amount of time during which the ointment stands at room temperature. Other larger filling equipment which is well known in the art can also be used.

To demonstrate that the heating of the interferon source liquid to 45° C. to facilitate it mixing with the polyethylene glycol mixture did not significantly decrease the activity of the interferon, a sample of crude concentrated alpha-interferon source liquid, prepared in accordance with Example 1, was heated to 45° C., held at that temperature for 1 hour, and then stored at −20° C. The changes in the titer of this sample over time were compared to those of an unheated sample. The titers of the heated and unheated interferon samples were essentially identical, thus establishing that the heating step used to prepare polyethylene glycol-based ointments does not destroy the biological activity of the interferon.

To compare the quality of an ointment produced by mixing the interferon and the polyethylene glycols at elevated temperature with the quality of an ointment produced by mechanical mixing of these components at room temperature, a batch of ointment was prepared by adding 45 milliliters of crude concentrated alpha-interferon source liquid to 300 grams of the 60:40 polyethylene glycol mixture, described above, which had been cooled to room temperature The two components were placed in a sealable plastic bag and the contents were mixed by kneading the bag by hand and rolling the bag using a cylindrical bar. The kneading and rolling was carried out for a period of approximately 30 minutes, after which the ointment was compared with the ointment prepared by heating, as described above. The mechanically mixed ointment was in general found to have a non-uniform color and consistency indicating that a homogeneous dispersion of the interferon throughout the polyethylene glycol mixture had not been achieved. In comparison, the ointment prepared by heating the interferon and the polyethylene glycols exhibited uniform color and consistency throughout the ointment.

EXAMPLE 6

Preparation of an Interferon Topical Ointment Having a HEC Vehicle Base

An interferon ointment having a hydroxyethyl cellulose vehicle base is prepared as follows (for 100 gms):

Preparation of Stock A

First, 2.5 grams of high viscosity hydroxyethyl cellulose (2200 centipoise) (Polysciences, Warrington, Pa.) are measured into a beaker. Aggregates of the hydroxyethyl cellulose powder are broken up. Next, 10.0 grams of USP glycerine are added to the hydroxyethyl cellulose powder and the two components are mixed to form a uniform slurry. Then 60.8 milliliters of purified water and 3.0 gm of redox system containing 1.5 gm HEC-cysteine (1% cysteine bound) reducing agent and 1.5 gm HEC-cystine (0.1% cystine bound) oxidizing agent are added to the hydroxyethyl cellulose/glycerine mixture. The water is then added. Thereafter, the solution is mixed rapidly until the gel thickens.

Preparation of Stock B 0.06 grams of propyl paraben and 0.25 grams of methyl paraben are added to 10 grams of sterile glycerin which is at approximately 65°-75° C. Care is taken to insure that the mixture does not reach a temperature above about 75° C. so as not to inactivate the propyl and methyl parabens. The parabens are mixed in the glycerin until no paraben powder is observed in the mixture. Stock B is then cooled to room temperature. At this time, stock A and stock B are mixed together to form a homogeneous gel. The mixture is then placed in an ice bath and cooled with mixing until a temperature of 4° C. is reached.

A sterile interferon stock solution is formulated as follows:

Thirteen milliliters of the foregoing sterile-filtered interferon stock solution are then combined with 0.52 milliliters of a 50 mg/ml, sterile-filtered, soybean trypsin inhibitor solution (Sigma Chemical Company, St. Louis, Mo.). This solution is then added to the cooled vehicle base/paraben mixture and the combination is mixed until a uniform dispersion is visually observed. The gel is then loaded into a tube filling machine (various types of this equipment are known to the art). The gel is dispensed into sterile aluminum ointment tubes which are then crimped closed.

What is claimed is:

1. A substantially non-toxic, stable, topical therapeutic composition which comprises:
   (a) a lymphokine which is susceptible to oxidative degradation;
   (b) an oxidative degradation-inhibitory amount of a redox system containing
      (1) a water soluble polymer containing a plurality of reducing moieties covalently bound thereto and
      (2) a water soluble polymer containing a plurality of oxidizing moieties covalently bound thereto; and,
   (c) an aqueous vehicle base compatible with the lymphokine which is capable of holding the lymphokine in suspension and releasing a therapeutically effective amount of lymphokine at the site of application.

2. The therapeutic composition of claim 1 wherein the lymphokine is one or more natural or recombinant interferons.

3. The therapeutic composition of claim 2 containing from about 10,000 to about 1,000,000 NIH units of interferon gram.

4. The therapeutic composition of claim 2 containing from about 25,000 to about 500,000 NIH units of interferon per gram.

5. The therapeutic composition of claim 1 wherein the water soluble polymer is derived from a polyethylene glycol of the formula $HO(CH_2CH_2O)_n H$ wherein n is from about 20 to about 225,000.

6. The therapeutic composition of claim 1 wherein the water soluble polymer is derived from hydroxyethyl cellulose.

7. The therapeutic composition of claim 1 wherein the reducing moieties are derived from cysteine or mercaptopropionic acid.

8. The therapeutic composition of claim 1 wherein the oxidizing moieties are derived from the oxidation of cysteine or mercaptopropionic acid ester moieties to provide cystine or dithiodipropionic acid ester, respectively.

9. The therapeutic composition of claim 1 wherein the vehicle base is a water soluble polyethylene glycol.

10. The therapeutic composition of claim 1 wherein the vehicle base is an aqueous hydroxyethyl cellulose.

11. A method for treating a body having a disease condition which is responsive to treatment by a lymphokine topically applied thereto which comprises topically applying to the body an amount of the composition of claim 1 which is effective to treat the disease condition.

12. The method for treating a body having a disease condition which is responsive to treatment by a lymphokine topically applied thereto which comprises topically applying to the body an amount of the composition of claim 2 which is effective to treat the disease condition.

13. A method for treating a body infected with herpes genitalis which comprises topically applying to skin lesions resulting from herpes genitalis infection a therapeutically effective amount of the composition of claim 2.

14. A method for inhibiting the oxidative degradation of a lymphokine susceptible thereto which comprises combining said lymphokine with an oxidative degradation-inhibiting amount of a redox system containing
   (a) a water soluble polymer containing a plurality of reducing moieties covalently bound thereto and
   (b) a water soluble polymer containing a plurality of oxidizing moieties covalently bound thereto.

15. The method of claim 14 wherein the lymphokine is a natural or recombinant interferon.

16. The method of claim 15 wherein the water soluble polymer is derived from a polyethylene glycol or a hydroxyethyl cellulose.

17. The method of claim 16 wherein the reducing moieties are derived from cysteine or mercaptopropionic acid.

18. The method of claim 16 wherein the oxidizing moieties are derived from cystine or dithiodipropionic acid.

* * * * *